United States Patent
Domb et al.

(10) Patent No.: US 11,141,488 B2
(45) Date of Patent: Oct. 12, 2021

(54) COMPOSITIONS COMPRISING BIODEGRADABLE COPOLYMERS FOR PROLONGED LOCAL RELEASE OF AN ANTIBIOTIC

(71) Applicant: DEXCEL PHARMA TECHNOLOGIES LTD., Or-Akiva (IL)

(72) Inventors: Abraham J. Domb, Jerusalem (IL); Michael Grishko, Nesher (IL); Ezra Hanuka, Nesher (IL); Ron Schlinger, Tel-Aviv (IL); Tal Hagigit, Moshav Gan Yoshiya (IL)

(73) Assignee: DEXCEL PHARMA TECHNOLOGIES LTD., Or-Akiva (IL)

( * ) Notice: Subject to any disclaimer, the term of this patent is extended or adjusted under 35 U.S.C. 154(b) by 111 days.

(21) Appl. No.: 16/497,137

(22) PCT Filed: Mar. 29, 2017

(86) PCT No.: PCT/IL2017/050389
§ 371 (c)(1),
(2) Date: Sep. 24, 2019

(87) PCT Pub. No.: WO2018/178963
PCT Pub. Date: Oct. 4, 2018

(65) Prior Publication Data
US 2020/0101163 A1     Apr. 2, 2020

(51) Int. Cl.
A61K 47/34     (2017.01)
A61K 9/00     (2006.01)
(Continued)

(52) U.S. Cl.
CPC ............ *A61K 47/34* (2013.01); *A61K 9/0019* (2013.01); *A61K 31/7036* (2013.01); *C08G 63/06* (2013.01)

(58) Field of Classification Search
CPC .. A61K 47/34; A61K 9/0019; A61K 31/7036; A61K 9/0024; C08G 63/06
See application file for complete search history.

(56) References Cited

U.S. PATENT DOCUMENTS

| 4,414,381 A | 11/1983 | Griffin |
| 4,999,417 A | 3/1991 | Domb |

(Continued)

FOREIGN PATENT DOCUMENTS

| EP | 0598131 A1 | 5/1994 |
| EP | 0892022 A1 | 1/1999 |

(Continued)

OTHER PUBLICATIONS

Haim-Zada et al, Stable Polyanhydride Synthesized from Sebacic Acid and Ricinoleic Acid, Journal of Controlled Release, 257: 156-162. (Year: 2017).*

(Continued)

*Primary Examiner* — Carlos A Azpuru
(74) *Attorney, Agent, or Firm* — Rothwell, Figg, Ernst & Manbeck, P.C.

(57) ABSTRACT

A depot system containing at least one antibiotic and a biodegradable poly(ester-anhydride) of ricinoleic acid (RA) and sebacic acid (SA) having alternating or semi-alternating ester and anhydride bonds is provided. The system provides prolonged local release of the antibiotic at the site of injection while maintaining the systemic antibiotic levels at sub-therapeutic concentrations.

21 Claims, 8 Drawing Sheets

(51) Int. Cl.
*A61K 31/7036* (2006.01)
*C08G 63/06* (2006.01)

(56) References Cited

U.S. PATENT DOCUMENTS

| | | | |
|---|---|---|---|
| 5,010,167 A | 4/1991 | Ron | |
| 5,109,107 A | 4/1992 | Vora | |
| 5,171,812 A | 12/1992 | Domb | |
| 5,179,189 A | 1/1993 | Domb | |
| 5,317,079 A | 5/1994 | Domb | |
| 5,473,103 A | 12/1995 | Domb | |
| 5,480,787 A | 1/1996 | Negishi | |
| 5,565,188 A | 10/1996 | Wong | |
| 5,626,862 A | 5/1997 | Brem | |
| 5,648,096 A | 7/1997 | Gander | |
| 5,756,652 A | 5/1998 | Storey | |
| 5,846,565 A | 12/1998 | Brem | |
| 5,859,271 A | 1/1999 | Franson | |
| 6,025,410 A | 2/2000 | Moy | |
| 6,303,138 B1 | 10/2001 | Peterson | |
| 6,306,403 B1 | 10/2001 | Donovan | |
| 7,297,347 B2 | 11/2007 | Domb | |
| 7,749,539 B2 | 7/2010 | Domb | |
| 8,575,092 B2 * | 11/2013 | Domb | A61K 9/0024 514/2.1 |
| 2004/0161464 A1 | 8/2004 | Domb | |
| 2009/0111732 A1 | 4/2009 | Domb | |

FOREIGN PATENT DOCUMENTS

| | | |
|---|---|---|
| EP | 0952171 A2 | 10/1999 |
| WO | 9015586 A2 | 12/1990 |
| WO | 9305096 A1 | 3/1993 |
| WO | 9622270 A1 | 7/1996 |
| WO | 9802171 A1 | 1/1998 |
| WO | 9912990 A1 | 3/1999 |
| WO | 0244232 A2 | 6/2002 |
| WO | 2005079861 A2 | 9/2005 |
| WO | 2007110694 A2 | 10/2007 |
| WO | 2016097848 A1 * | 6/2016 |

OTHER PUBLICATIONS

Bremer and Osmundsen, "Fatty Acid Oxidation and Its Regulation in Fatty Acid Metabolism and Its Regulation" (Numa ed.), 1984. Elsevir, New York; pp. 113-154.
Dang et al., (1996) Effects of GLIADEL® wafer initial molecular weight on the erosion of wafer and release of BCNU. Journal of Controlled Release 42(1): 83-92.
Domb and Langer (1987) Polyanhydrides. I. Preparation of high molecular weight polyanhydrides. Journal of Polymer Science Part A: Polymer Chemistry 25(12): 3373-3386.
Domb and Maniar (1993) Absorbable biopolymers derived from dimer fatty acids. Journal of Polymer Science Part A: Polymer Chemistry 31(5): 1275-1285.
Domb et al., (1989) Poly(anhydrides). 3. Poly(anhydrides) based on aliphatic-aromatic diacids. Macromolecules 22(8): 3200-3204.
Domb et al., (1998) Biopolymers as drug carriers and bioactive macromolecules. Acta Polymerica 49 (10-11): 526-533.
Domb et al., "Polyanhydrides". In: Handbook of Biodegradable Polymers (Domb et al., Eds.), Harwood Academic Publishers, 1997; pp. 135-159.
Domb et al., (2005) Biodegradable Polymers Derived from Fatty Acids. Proceedings of the 8th Polymer for Advanced Technologies International Symposium. Budapest, Hungary. Sep. 13-16, 2005. 2 pages.
Gopferich, Mechanism of Polymer Degradation and Elimination in Handbook of Biodegradable Polymers (Domb et al., Eds.), Harwod Academic Publishers, 1997; pp. 451-471.
Haim-Zada et al., (2016) Alternating Poly(ester-anhydride) by Insertion Polycondensation. Biomacromolecules 17(6): 2253-2259.
Haim-Zada et al., (2017) Stable polyanhydride synthesized from sebacic acid and ricinoleic acid. Journal of Controlled Release 257: 156-162.
Heller (1984) Biodegradable polymers in controlled drug delivery. Critical Reviews in Therapeutic Drug Carrier Systems 1(1): 39-90.
Hiremath et al., (2008) Biodegradable poly(sebacic acid-co-ricinoleic-ester anhydride) tamoxifen citrate implants: Preparation and in vitro characterization. Journal of Applied Polymer Science 107(5): 2745-2754.
Hopfenberg, Controlled Release From Erodible Slabs, Cylinders, and Spheres in Controlled Release Polymeric Formulations (Paul et al., Eds.) ACS Symposium Series, Washington DC, 1976 33: 26-32.
Krasko and Domb (2005) Hydrolytic Degradation of Ricinoleic-Sebacic-Ester-Anhydride Copolymers. Biomacromolecules 6(4): 1877-1884.
Krasko and Domb (2007) Pasty injectable biodegradable polymers derived from natural acids. Journal of Biomedical Materials Research Part A 83A(4): 1138-1145.
Krasko et al., (2003) Poly(ester anhydride)s prepared by the insertion of ricinoleic acid into poly(sebacic acid). Journal of Polymer Science Part A: Polymer Chemistry 41(8): 1059-1069.
Krasko et al., (2007) Gentamicin extended release from an injectable polymeric implant. Journal of Controlled Release 117(1): 90-96.
Leong et al., (1986) Polyanhydrides for controlled release of bioactive agents. Biomaterials 7(5): 364-371.
Mäder et al., (1997) In Vitro/In Vivo Comparison of Drug Release and Polymer Erosion from Biodegradable P(FAD-SA) Polyanhydrides—A Noninvasive Approach by the Combined Use of Electron Paramagnetic Resonance Spectroscopy and Nuclear Magnetic Resonance Imaging. Pharmaceutical Research 14(6): 820-826.
O'Hagan (1998) Microparticles and polymers for the mucosal delivery of vaccines. Advanced Drug Delivery Reviews 34(2-3): 305-320.
Park et al., (1998) Biodegradable polyanhydride devices of cefazolin sodium, bupivacaine, and taxol for local drug delivery: preparation, and kinetics and mechanism of in vitro release. Journal of Controlled Release 52(1-2): 179-189.
Rosen et al., (1983) Bioerodible polyanhydrides for controlled drug delivery. Biomaterials 4(2): 131-133.
Shikanov and Domb (2006) Poly(sebacic acid-co-ricinoleic acid) Biodegradable Injectable in Situ Gelling Polymer. Biomacromolecules 7(1): 288-296.
Shikanov et al., (2004) Poly(sebacic acid-co-ricinoleic acid) biodegradable carrier for paclitaxel: In vitro release and in vivo toxicity. Journal of Biomedical Materials Research Part A 69A(1): 47-54.
Shikanov et al., (2005) Poly(sebacic acid-co-ricinoleic acid) biodegradable carrier for paclitaxel—effect of additives. Journal of Controlled Release 105(1-2): 52-67.
Teomim and Domb (1999) Fatty acid terminated polyanhydrides. Journal of Polymer Science Part A: Polymer Chemistry 37(16): 3337-3344.
Teomim et al., (1999) Perivascular delivery of heparin for the reduction of smooth muscle cell proliferation after endothelial injury. Journal of Controlled Release 60(1): 129-142.
Teomim et al., (1999) Ricinoleic acid-based biopolymers. Journal of Biomedical Materials Research 45(3): 258-267.
Tirosh et al., (1997) Oxidative stress effect on the integrity of lipid bilayers is modulated by cholesterol level of bilayers. Chemistry and Physics of Lipids 87(1): 17-22.

* cited by examiner

COMPOSITIONS COMPRISING BIODEGRADABLE COPOLYMERS FOR PROLONGED LOCAL RELEASE OF AN ANTIBIOTIC

TECHNICAL FIELD

A parenteral pharmaceutical composition comprising an antibiotic or combination of antibiotics is provided. The parenteral pharmaceutical composition is preferably a depot system for prolonged local release of the antibiotic(s) at the site of injection.

BACKGROUND

Biodegradable polymers suitable for local and/or systemic drug delivery are advantageous because they obviate the need for additional medical intervention for removal of non-degradable drug depleted devices. These polymers and their degradation components must possess several attributes including compatibility with biological tissues, negligible toxicity and easy elimination from the body. Biodegradable polymers are generally hydrophobic thereby maintaining their integrity in physiological environments after administration.

Many biodegradable polymers have been evaluated for use as implantable controlled drug release matrices, including polyesters, polycarbonates, natural and synthetic polyamides, polyphosphate esters, polyphosphazenes and polyanhydrides. Biodegradable polyesters based on polylactic acid and copolymers of lactide and glycolide are the most common polymers used in biodegradable dosage forms.

Poly(ester-anhydrides) formed from ricinoleic acid and natural fatty diacids have been disclosed in U.S. Pat. Nos. 7,297,347 and 7,749,539. These polymers may be admixed with a variety of bioactive agents including small drug molecules, peptides and proteins. The drug delivery compositions are administered to a patient in a liquid, gel or paste form and are able to release the incorporated bioactive agent over several days and even weeks.

The polymers described in U.S. Pat. Nos. 7,297,347 and 7,749,539 are composed of a random sequence of ricinoleic acid having dual functionality and fatty diacids (for example sebacic acid). These polymers do not exhibit consistent stability and other properties over the bulk of the material to enable them to act as robust biodegradable polymers for prolonged drug delivery.

WO 2016/097848 discloses a copolymer characterized by alternating or semi-alternating ester and anhydride bonds, methods for its production and use thereof, particularly as a carrier for drug delivery. The copolymer is characterized by reproducible product specifications including controlled viscosity and molecular weight and is shown to be stable for months at room temperatures.

Haim-Zada, et al., *Biomacromolecules.* 2016 Jun. 13; 17(6):2253-9 disclose a synthetic method for preparing alternating poly(ester-anhydride) copolymers where polyanhydride is used as starting material and the ester monomers are inserted through complete esterification.

Haim-Zada, et al., *J Control Release.* 2016 Apr. 25; pii: S0168-3659 (16)30250-4, doi: 10.1016/j.jconrel.2016.04.036 disclose stable polyanhydride synthesized from sebacic acid and ricinoleic acid.

There is an unmet medical need for compositions comprising biodegradable polymers for the prolonged local release of an active agent, e.g. antibiotics.

SUMMARY OF THE INVENTION

The present disclosure relates to a parenteral pharmaceutical composition comprising a biodegradable poly(ester-anhydride) copolymer of ricinoleic acid (RA) and sebacic acid (SA) having alternating or semi-alternating ester and anhydride bonds and an antibiotic that is released locally in a continuous manner.

The composition described herein affords the local in vivo release of a therapeutically effective amount of the antibiotic(s) for prolonged period of time while keeping the systemic levels sub-therapeutic or negligible. The composition therefore provides reduced incidence of adverse events and/or reduced severity of adverse events of the antibiotic(s) at the local and/or systemic level.

According to a first aspect, there is provided a parenteral pharmaceutical composition comprising a biodegradable poly(ester-anhydride) copolymer of ricinoleic acid (RA) and sebacic acid (SA) having alternating or semi-alternating ester and anhydride bonds and an antibiotic, the composition being a sustained release depot system which releases a local therapeutically effective amount of the antibiotic over a period of about 1 day to about 20 weeks, wherein 24 hours or more after a single parenteral administration, the systemic level of the antibiotic or metabolite thereof is about 10 µg/ml or less. In one embodiment, the systemic level of the antibiotic or metabolite thereof 24 hours or more after a single parenteral administration is about 5 µg/ml or less. In another embodiment, the systemic level of the antibiotic or metabolite thereof 24 hours or more after a single parenteral administration is about 1 µg/ml or less.

In certain embodiments, the composition releases a local therapeutically effective amount of the antibiotic over a period of about 1 week to about 8 weeks, including each integer within the specified range.

According to various embodiments, the concentration of the antibiotic in the composition is in the range of between about 1% and about 50% (w/w), including each integer within the specified range. In exemplary embodiments, the concentration of the antibiotic in the composition is in the range of between about 5% and about 30% (w/w), including each integer within the specified range. In particular embodiments, the concentration of the antibiotic in the composition is about 10% (w/w). In other embodiments, the concentration of the antibiotic in the composition is about 20% (w/w).

In further embodiments, the antibiotic is an aminoglycoside.

In some embodiments, the aminoglycoside is at least one of kanamycin A, amikacin, tobramycin, dibekacin, gentamicin, sisomicin, netilmicin, neomycins B, C or E, and streptomycin or pharmaceutically acceptable salts thereof. Each possibility represents a separate embodiment. In particular embodiments, the aminoglycoside is gentamicin or a pharmaceutically acceptable salt thereof (e.g. gentamicin sulfate).

In other embodiments, the antibiotic is at least one of apramycin, arbekacin, astromicin, bekanamycin, dihydrostreptomycin, elsamitrucin, fosfomycin/tobramycin, G418, hygromycin B, isepamicin, kasugamycin, legonmycin, lividomycin micronomicin, neamine, nourseothricin, paromomycin, plazomicin, ribostamycin, streptoduocin, totomycin, and verdamicin. Each possibility represents a separate embodiment. In further embodiments, the antibiotic is at least one of ampicillin, norfloxacin, sulfamethoxazole, flumequine, and amphotericin B. Each possibility represents a separate embodiment.

In another aspect, there is provided a parenteral pharmaceutical composition comprising a biodegradable poly(ester-anhydride) copolymer of ricinoleic acid (RA) and sebacic acid (SA) having alternating or semi-alternating ester and anhydride bonds and gentamicin or a pharmaceutically acceptable salt thereof, the composition providing an in-vitro release of not more than about 20% of gentamicin in 25 days in 1 ml of 0.1M phosphate buffer at pH 7.4, 100 rpm and 37° C.

The pharmaceutical composition described herein is designed as a parenteral composition. In one embodiment, the parenteral administration comprises subcutaneous injection. In another embodiment, the parenteral administration comprises intramuscular injection. In yet another embodiment, the parenteral administration comprises intraosseous injection. In further embodiments, the parenteral administration comprises periosteal injection.

In certain embodiments, the poly(ester-anhydride) copolymer has a monomer ratio of ricinoleic acid to sebacic acid in the range of from about 60:40 to about 80:20 (w/w), including all iterations of ratios within the specified range. In particular embodiments, the copolymer has a monomer ratio of ricinoleic acid to sebacic acid in the range of from about 65:35 to about 80:20 (w/w), including all iterations of ratios within the specified range. In one embodiment, the copolymer has a monomer ratio of ricinoleic acid to sebacic acid of about 67:33 (w/w). In another embodiment, the copolymer has a monomer ratio of ricinoleic acid to sebacic acid of about 70:30 (w/w). In yet another embodiment, the copolymer has a monomer ratio of ricinoleic acid to sebacic acid of about 77:23 (w/w).

In additional embodiments, the copolymer in the composition has an average molecular weight of from about 2,000 to about 50,000 daltons, including each integer within the specified range. In specific embodiments, the copolymer in the composition has an average molecular weight of from about 8,000 to about 20,000 daltons, including each integer within the specified range.

It is contemplated that the copolymer in the composition is degraded at a slower rate than the local or systemic release rate of the antibiotic.

In certain embodiments, the composition is useful for the treatment of osteomyelitis or the reduction of the occurrence of osteomyelitis, particularly in a subject having an open bone fracture. Thus, in one embodiment, there is provided a method of treating osteomyelitis in a subject in need thereof, the method comprising the step of parenterally administering to the subject the composition of the disclosure. In other embodiments, there is provided a method of reducing the occurrence of osteomyelitis in a subject having an open bone fracture comprising the step of parenterally administering to the subject the composition of the disclosure. In additional embodiments, there is provided a method of reducing the occurrence of soft tissue infection in a subject having an open bone fracture comprising the step of parenterally administering to the subject the composition of the disclosure.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
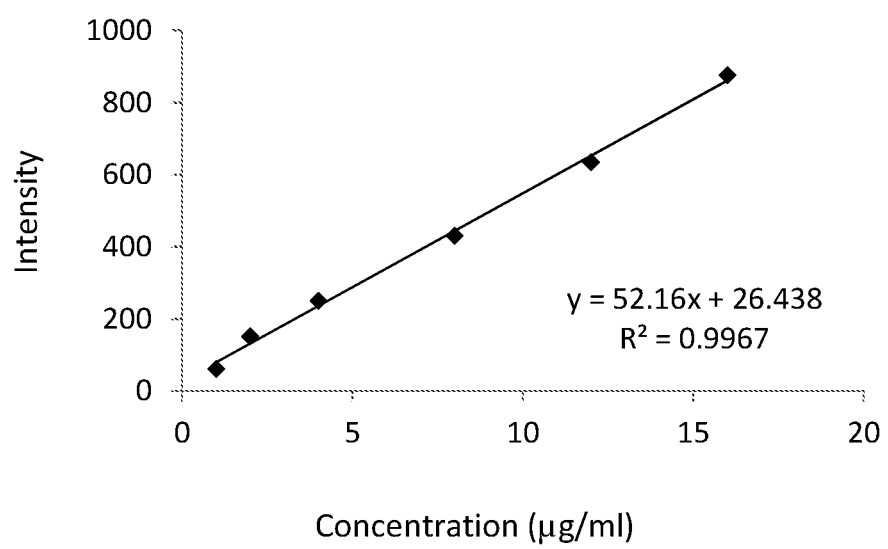
FIG. 1. Calibration curve for gentamicin measured using a spectrofluorometer at excitation wavelength of 390 nm and emission wavelength of 460 nm.

There is provided a pharmaceutical composition which forms a depot system providing prolonged local release of an active pharmaceutical agent while affording negligible (sub-therapeutic) systemic levels of the active pharmaceutical agent 24 hours or more after administration of a single dose. Accordingly, therapeutic efficacy at the site of administration is achieved and, at the same time, adverse systemic effects are avoided. Hence, the pharmaceutical composition described herein provides reduced incidence of adverse events or reduced severity of adverse events of the active pharmaceutical agent at the local or systemic level.

According to certain aspects and embodiments, there is provided a parenteral pharmaceutical composition comprising an active pharmaceutical agent. The parenteral composition is in depot form suitable for injection or implantation at a medically acceptable location in a subject in need thereof. The term "parenteral" as used herein refers to routes of administration including, but not limited to, subcutaneous (SC), intramuscular (IM), intradermal (ID), intraperitoneal (IP), intraosseous (IO), intraarticular, intravesical, periosteal and the like. Each possibility represents a separate embodiment.

The pharmaceutical composition described herein is a long acting pharmaceutical composition. The term "long acting" as used herein refers to a composition which provides continuous release, i.e. prolonged, sustained and/or extended release of the active agent at local sites of action in a subject. This term may further refer to a composition which provides prolonged, sustained and/or extended duration of action (pharmacokinetics) of the active agent at a local site of action in a subject. Thus, according to some embodiments, the composition releases a therapeutically effective amount of the active agent at a local site of action over a period of about one day to about twenty weeks. For example, the composition may release a therapeutically effective amount of the active agent at a local site of action for about 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, or 20 weeks, with each possibility representing a separate embodiment. In specific embodiments, the composition releases a therapeutically effective amount of the active agent at a local site of action over a period of about one week to about eight weeks.

The term "local" as used herein refers to a radius of about 0 to about 10 cm from the site of injection of a therapeutically effective amount of the active agent. For example, the radius in which a therapeutically effective amount of the active agent can be found includes a range of from about 0 to about 6 cm, including each integer within the specified range. It is contemplated that parenteral administration can be performed in several adjacent sites thereby resulting in a broader area of therapy. Within the scope of the disclosure is the single parenteral administration of the composition to obtain physical coverage of a target tissue.

While the pharmaceutical composition of the disclosure provides a therapeutic effective amount of the active agent for prolonged duration at a local site of action, the systemic levels of the active agent 24 hours or more after parenteral administration are sub-therapeutic.

According to certain aspects and embodiments, the parenteral pharmaceutical composition described herein provides an in-vitro release profile of the active pharmaceutical agent corresponding to not more than about 20% in 25 days in 1 ml of 0.1M phosphate buffer at pH 7.4, 100 rpm and 37° C. The in-vitro release can be quantified as is known in the art, for example using spectrofluorometer.

According to various aspects and embodiments, there is provided a pharmaceutical composition comprising a biodegradable poly(ester-anhydride) having alternating or semi-alternating ester and anhydride bonds.

Thus, in some aspects and embodiments, a parenteral pharmaceutical composition is provided, the composition comprising (a) a biodegradable poly(ester-anhydride) copolymer of Formula (1) having alternating or semi-alternating ester and anhydride bonds; and (b) an active pharmaceutical agent, the composition being a sustained release depot system which releases a local therapeutically effective amount of the active pharmaceutical agent over a period of about 1 day to about 20 weeks, wherein 24 hours or more after a single parenteral administration the systemic level of the active pharmaceutical agent or metabolite thereof is about 10 µg/ml or less.

In other aspects and embodiments, there is provided a parenteral pharmaceutical composition comprising (a) a biodegradable poly(ester-anhydride) copolymer of Formula (1) having alternating or semi-alternating ester and anhydride bonds; and (b) an active pharmaceutical agent, the composition providing an in-vitro release of not more than about 20% of the active pharmaceutical agent in 25 days in 1 ml of 0.1M phosphate buffer at pH 7.4, 100 rpm and 37° C.

In additional aspects and embodiments, there is provided a parenteral pharmaceutical composition comprising (a) a biodegradable poly(ester-anhydride) copolymer of Formula (1) having alternating or semi-alternating ester and anhydride bonds; and (b) an active pharmaceutical agent, the composition providing an in-vitro release of not more than about 40% of the active pharmaceutical agent in 40 days in 5 ml of phosphate buffer at pH 7.4, 30 rpm and 37° C.

The poly(ester-anhydride) having alternating or semi-alternating ester and anhydride bonds of Formula (1) includes, but is not limited to, copolymers described in WO 2016/097848, the contents of which are incorporated by reference herein in their entirety as if fully set forth herein.

The structure of the copolymers of Formula (1) is represented below:

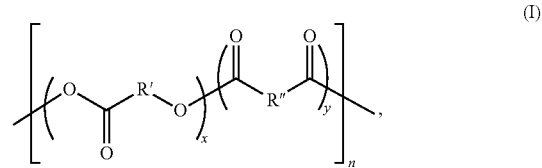

wherein R' and R" are independently selected from the group consisting of linear or branched $C_1$-$C_{40}$ alkylene, $C_2$-$C_{40}$ alkenylene, and $C_2$-$C_{40}$ alkynylene, and wherein each x and y is independently an integer from 1 to 5 provided that x+y is not greater than 6, and n is an integer from about 2 to about 1,000, including each integer within the specified range.

In some embodiments, x+y is equal to 2, 3 or 5. Each possibility represents a separate embodiment. In specific embodiments, x is 1 and y is 1, or x is 2 and y is 1.

It is contemplated that the poly(ester-anhydride) copolymer comprises alternating or semi-alternating sequence of monomeric units. In one embodiment, the alternating sequence comprises a repeating trimeric unit. In other embodiments, the semi-alternating sequence comprises a repeating dimeric unit. In yet other embodiments, the semi-alternating sequence comprises two repeating units, i.e. a trimeric unit and a dimeric unit.

In one embodiment, the alternating sequence comprises the following repeating trimeric unit:

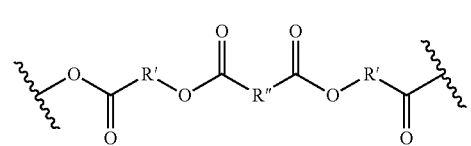

The above formula may further be designated by the formula -(ABA)-, wherein A represents the R' containing monomeric unit, and B represents the R" containing monomeric unit. The monomeric units are linked by two consecutive ester bonds. Using this formula, the copolymer has an alternating sequence which may be depicted:

-[-(ABA)-(ABA)-(ABA)-(ABA)-]-

In another embodiment, the semi-alternating sequence of the poly(ester-anhydride) copolymer contains the following repeating dimeric unit in which the monomeric units are linked by an ester bond:

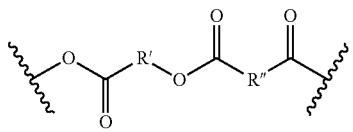

In accordance with these embodiments, the poly(ester-anhydride) copolymer comprises semi-alternating sequence of repeating dimeric units which may be -(A-B)-(A-B)- ("head-to-tail"); -(B-A)-(A-B)- ("head-to-head"); -(A-B)-(B-A)- ("tail-to-tail") or a combination thereof. In certain embodiments, a copolymer containing the repeating dimeric unit comprises an equivalent amount of the three linkages described above. It will be recognized, however, that the choice of R' and R" may result in steric hindrance thereby favoring one of the three linkages described above.

The poly(ester-anhydride) may comprise a sequence of the trimeric unit, a sequence of the dimeric unit, or a sequence of a mixture of the trimeric and dimeric units. As used herein, "a poly(ester-anhydride) containing a sequence of the trimeric unit" refers to a polymer in which at least about 90%, preferably at least about 95%, more preferably at least about 97.5%, and even more preferably at least substantially all of its sequence is composed of the repeating trimeric unit. Similarly, the phrase "a poly(ester-anhydride) containing a sequence of the dimeric unit" refers to a polymer in which at least about 90%, preferably at least about 95%, more preferably at least about 97.5%, and even more preferably at least substantially all of its sequence is composed of the repeating dimeric unit. The units may be arranged in a periodic or semi-periodic sequence thereby resulting in a poly(ester-anhydride) containing alternating or semi-alternating monomeric units.

In some aspects and embodiments, where x and y, independently for each occurrence, is an integer selected from 1 and 2, the poly(ester-anhydride) of Formula (1) is characterized by the substantial absence of two or more consecutive anhydride bonds between the monomeric units along its structure. In accordance with these embodiments, the poly(ester-anhydride) comprises less than about 10 mole %, preferably less than about 5 mole %, and more preferably less than about 2.5 mole % of two or more consecutive anhydride bonds between the monomeric units along its structure.

In certain embodiments, the poly(ester-anhydride) has the structure of Formula (2):

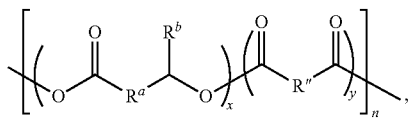

(2)

wherein R", x, y and n are as defined above, $R^a$ is a $C_2$-$C_{20}$ alkenylene, and $R^b$ is a $C_1$-$C_{10}$ alkyl.

For certain embodiments in which $R^a$ is $C_2$-$C_{20}$ alkenylene, $R^a$ may be represented by the formula:

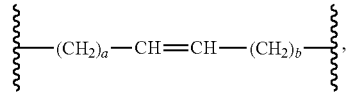

wherein a and b are selected from 0-18, provided that a+b is equal to or less than 18. The $(CH_2)_a$ unit is further connected to the carbonyl and the $(CH_2)_b$ unit is further connected to the oxygen atom. The double bond may have a cis or trans configuration, with each possibility representing a separate embodiment. Suitable a in the aforementioned formula may be selected from 1-12, preferably 1-10, more preferably 2-10, even more preferably 4-10, and suitable b may be selected from 0-6, preferably 1-6, and even more preferably 1-4.

In some embodiments, R" is a linear, unsubstituted $C_1$-$C_{12}$ alkylene group, preferably $C_2$-$C_{10}$, more preferably $C_4$-$C_{10}$, and even more preferably a linear, unsubstituted $C_6$-$C_8$ alkylene group.

As used herein, affixing the suffix "-ene" to a group indicates that the group is a divalent moiety, e.g., alkylene is the divalent moiety of alkyl, alkenylene is the divalent moiety of alkenyl, and so forth.

According to particular aspects and embodiments, the poly(ester-anhydride) copolymer used in the pharmaceutical composition described herein is a copolymer of ricinoleic acid (RA) and sebacic acid (SA), typically at weight percent ratios in the range of from about 60:40 to about 80:20, including all iterations of ratios within the specified range. In one embodiment, the weight percent ratio of the ricinoleic acid (RA) to sebacic acid (SA) is about 65:35 to about 80:20, including all iterations of ratios within the specified range. In yet other embodiments, the weight percent ratio of the ricinoleic acid (RA) to sebacic acid (SA) is about 67:37. In further embodiments, the weight percent ratio of the ricinoleic acid (RA) to sebacic acid (SA) is about 70:30. In additional embodiments, the weight percent ratio of ricinoleic acid (RA) to sebacic acid (SA) is about 77:23.

As used herein and in the appended claims, the poly (ester-anhydride) copolymer may be represented by Formula (1), wherein R' is a $C_{11}$ alkenylene having a $C_6$-alkyl on the carbon carrying the O of the ester bond, i.e. $C_6$-alkyl-$C_{11}$ alkenylene; and wherein R" is a linear $C_8$-alkylene. Alternative representation of the copolymer is represented by the structure of Formula (2), wherein R" is a linear $C_8$-alkylene, $R^a$ is a $C_{10}$-alkenylene, and $R^b$ is a $C_6$-alkyl. It is contemplated that the double bond of the $C_{10}$-alkenylene may be in any position along the chain, preferably β-γ to the —O— of the ester bond. In currently preferred embodiments, $R^a$ is represented by the formula:

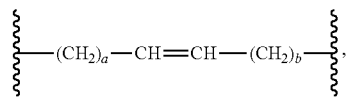

wherein a is 1 and the olefin is in the cis configuration.

The poly(ester-anhydride) copolymers may have molecular weights in the range of from about 2,000 to about 50,000 daltons depending on the polymerization conditions and the ratio between the components of the starting materials, including each integer within the specified range. In particular embodiments, the poly(ester-anhydride) copolymers may have molecular weights in the range of from about 8,000 to about 20,000 daltons, including each integer within the specified range. Exemplary non-limiting molecular weights include about 2,000, about 3,000, about 4,000, about 5,000, about 6,000, about 7,000, about 8,000, about 9,000, about 10,000, about 11,000, about 12,000, about 13,000, about 14,000, about 15,000, about 16,000, about 17,000, about 18,000, about 19,000, about 20,000, about 21,000, about 22,000, about 23,000, about 24,000, about 25,000, about 26,000, about 27,000, about 28,000, about 29,000, about 30,000, about 31,000, about 32,000, about 33,000, about 34,000, about 35,000, about 36,000, about 37,000, about 38,000, about 39,000, about 40,000, about 41,000, about 42,000, about 43,000, about 44,000, about 45,000, about 46,000, about 47,000, about 48,000, about 49,000, or about 50,000 daltons. Each possibility represents a separate embodiment. The determination of molecular weight can be performed as is known in the art, for example using gel-permeation chromatography (GPC). The viscosity of the obtained copolymer can be adjusted according to its methods of use. In particular embodiments, the copolymer is in liquid, semi-liquid or gel form at room temperatures thus being particularly suitable for administration via injection.

It is contemplated that the poly(ester-anhydride) having alternating or semi-alternating ester and anhydride bonds exhibits unexpected hydrolytic and storage stability, even when stored at 5° or 25° C. and 60% relative humidity (RH) for a period of months. The stability may be assessed by determining the molecular weight of the copolymer under accelerated stability conditions. In some embodiments, the molecular weight of the copolymer is decreased in less than about 25%, less than about 20%, less than about 15% or even less than about 10%, when the copolymer is stored at 25°/60% RH, 5° or −20° C. for 6 months, preferably for 12 months and more preferably for 18 months. The copolymer is designed to be degraded in-vivo at a slower rate than the local and/or systemic release period of the active agent.

The poly(ester-anhydride) copolymer can be prepared according to known methods. In some embodiments, the poly(ester-anhydride) copolymer may be prepared from a hydroxy-acid of Formula (3) (e.g. ricinoleic acid) and a diacid of Formula (4) (e.g. sebacic acid):

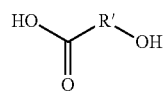

Formula (3)

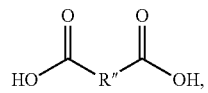

Formula (4)

wherein R' and R" are as defined above. By controlling the relative ratio of the compounds of Formula (3) and Formula (4) as well as the reaction conditions, either an alternating or semi-alternating poly(ester-anhydride) may be obtained. In one embodiment, the molar ratio of the monomers of Formula (3) to the monomers of Formula (4) ranges from about 5:1 to about 1:5, including all iterations of ratios within the specified range. In other embodiments, the molar ratio of the monomers of Formula (3) to the monomers of Formula (4) is about 2:1. In accordance with these embodiments, the copolymer has an alternating sequence containing a repeating trimeric unit as detailed above. In yet other embodiments, the molar ratio of the monomers of Formula (3) to the monomers of Formula (4) is about 1:1. In accordance with these embodiments, the copolymer has a semi-alternating sequence containing a repeating dimeric unit as detailed above. In additional embodiments, the molar ratio of the monomers of Formula (3) to the monomers of Formula (4) is about 1.5:1. In accordance with these embodiments, the copolymer has a semi-alternating sequence containing two repeating units containing about 1:1 ratio of a repeating trimeric unit and a repeating dimeric unit as detailed above. It will be recognized that other stoichiometric ratios may also be employed to provide alternating and/or semi-alternating copolymer.

The hydroxy-acid of Formula (3) and the diacid of Formula (4) can be obtained from readily available commercial suppliers or synthesized or extracted by standard methods. In one embodiment, the hydroxy-acid of Formula (3) is a hydroxy fatty acid. Suitable hydroxy acids include, but are not limited to, ricinoleic acid, hydroxy stearic acid, γ-hydroxy fatty acid such as 10-hydroxy dodecanoic acid, and the like. Each possibility represents a separate embodiment. The hydroxy fatty acids can be obtained from a natural or synthetic source. In a specific embodiment, the hydroxy-acid of Formula (3) is ricinoleic acid. In another specific embodiment, the ricinoleic acid is produced from castor oil as described in U.S. Pat. Nos. 7,297,347, 7,749,539, and 8,575,092, the content of each of which is hereby incorporated by reference.

The dicarboxylic acid (diacid) of Formula (4), according to certain embodiments, is selected from the group consisting of dodecanedioic acid, undecanedioic acid, sebacic acid, azelaic acid, suberic acid, pimelic acid, adipic acid, glutaric acid, succinic acid, and diabolic acids. Each possibility represents a separate embodiment. In a specific embodiment, the diacid of Formula (4) is sebacic acid.

In certain embodiments, the poly(ester-anhydride) copolymer is prepared by:
a) activating a compound of Formula (4)

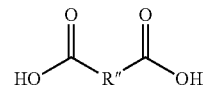

b) reacting the activated compound of Formula (4) obtained in step (a) with a compound of Formula (3)

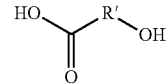

to give a repeating unit comprising a compound of Formula (1a)

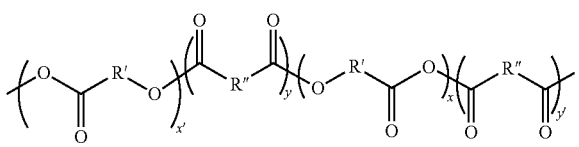

wherein x, y, R' and R" are as defined above; x' and y' is independently an integer from 0 to 5, provided that x'+y' is not greater than 6; and c) converting the repeating unit obtained in step (b) to an alternating or semi-alternating poly(ester-anhydride) copolymer of Formula (1).

The activating agent in step (a) may be any compound that enhances the reactivity of the carboxylic acid to anhydride formation. Suitable activating agents include, but are not limited to, acetic anhydride, propionic anhydride, phosgene, diphosgene, oxalyl chloride, acetyl chloride and thionyl chloride. Each possibility represents a separate embodiment. In one embodiment, the activating agent is acetic anhydride.

In certain embodiments, the reaction of the compound of Formula (4) with an activating agent produces a compound of Formula (4a):

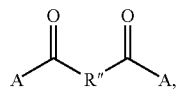
(4a)

wherein R" is as defined above, and A is selected from, for example: Cl, ClCOO, $CH_3COO$, $CH_3CH_2COO$ and the like. Each possibility represents a separate embodiment; or a polyanhydride of Formula (4p):

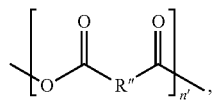
(4p)

wherein R" is as defined above, and n' is an integer selected from about 2 to about 500, preferably from about 5 to about 250, including each integer within the specified range.

Alternatively, the activated compound of Formula (4a) or (4p) can be obtained from commercial sources. It will be recognized that obtaining the activated compound of Formula (4a) or (4p) from commercial sources obviates the need for the step of activating a compound of Formula (4) in the method described above.

The activated compound of Formula (4) is reacted with the compound of Formula (3) under conditions sufficient to form an ester bond. According to certain aspects and embodiments, the esterification may be conducted by applying heat, vacuum or combinations thereof for a period of time sufficient so that the compound of Formula (3) is substantially consumed. In some embodiments, at least about 90% of the compound of Formula (3) is consumed in the reaction. In other embodiments, at least about 95% of the compound of Formula (3) is consumed in the reaction. In yet other embodiments, at least about 97.5% of the compound of Formula (3) is consumed in the reaction. The consumption of the compound of Formula (3) can be monitored throughout the reaction using analytical techniques such as $^1$H or $^{13}$C NMR, mass spectroscopy, FT-IR, UV-VIS, or chromatography quantification as is known in the art. For example, the consumption can be monitored using $^1$H NMR by showing the disappearance of the peak which corresponds to the proton located at the carbon attached to the hydroxyl group. Additionally and alternatively, the consumption of the compound of Formula (3) can be assessed by testing the structure of the formed polymer, for example by determining the presence of the acetylated terminus of the compound of Formula (3). Typically, the formed polymer is characterized by having less than about 2% acetylated terminus of the compound of Formula (3).

The esterification reaction is preferably conducted at a temperature of about 120-200° C., preferably about 150-180° C., and even more preferably at a temperature of about 160-180° C., including each integer within the specified ranges. Generally, the reaction is carried out for a period of several hours, depending on the batch size, mixing, reaction vessel and the ratio of the components of the starting materials.

The step of converting the repeating unit obtained in step (b) to an alternating or semi-alternating poly(ester-anhydride) copolymer of Formula (1) can be performed by treatment with an activating agent under conditions sufficient to form the poly(ester-anhydride) copolymer. Suitable activating agents include, but are not limited to, acetic anhydride, propionic anhydride, phosgene, diphosgene, oxalyl chloride, acetyl chloride and thionyl chloride. Each possibility represents a separate embodiment. In one embodiment, the activating agent is acetic anhydride. The reaction mixture may be heated, optionally with the application of vacuum, for a period of time sufficient to form the poly(ester-anhydride) copolymer having the desired molecular weight. The reaction is preferably conducted at a temperature of about 100-200° C., preferably about 110-180° C., and even more preferably at a temperature of about 130-150° C., including each integer within the specified ranges. For embodiments in which vacuum is applied, it is preferred that the vacuum is from about 0.01 to about 100 mm Hg, preferably from about 0.5 to about 50 mm Hg, and more preferably from about 15 to about 30 mm Hg, which is the vacuum range available in industrial settings for large scale equipment.

The work-up treatment in each step can be applied by typical methods, wherein isolation and purification is performed as necessary by selecting or combining conventional methods, such as precipitation in non-solvent, extraction, crystallization, recrystallization, distillation, partitioning, chromatography, preparative HPLC and the like. Each possibility represents a separate embodiment.

It is to be understood that although the aforementioned Formulae are drawn in a specific configuration, it is contemplated that the copolymer, monomers, and repeating units encompass all configurations, independently at each occurrence.

An exemplary, non-limiting process for producing alternating or semi-alternating poly(ester-anhydride) from ricinoleic acid and sebacic acid is illustrated in Scheme 1 below:

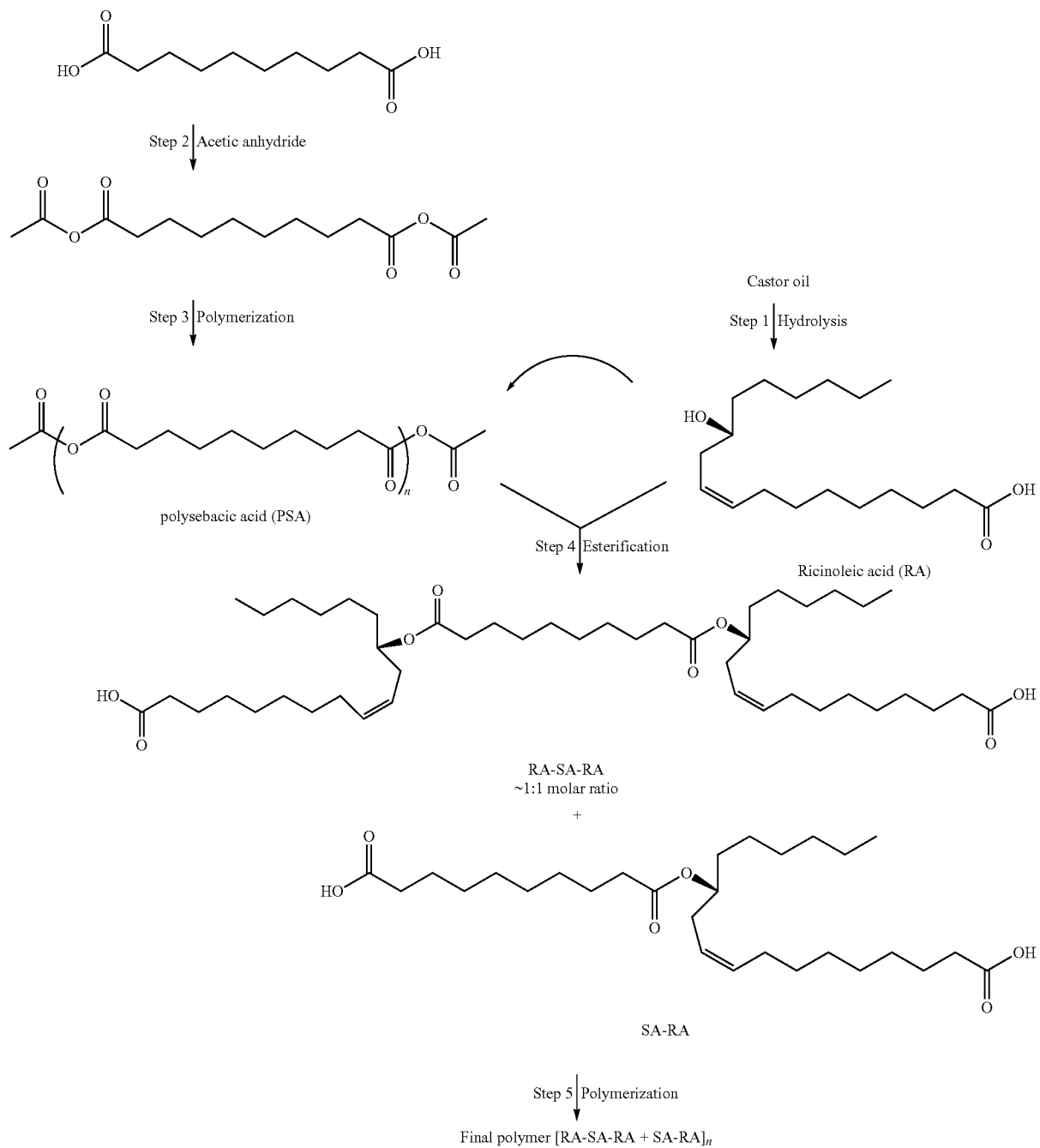

It is contemplated that the composition described herein may incorporate any active pharmaceutical agent to afford its prolonged release in a local site of action of a subject. Exemplary active pharmaceutical agents include, but are not limited to, analeptic agents, analgesic agents, anesthetic agents, antacid agents, antiasthmatic agents, antiarthritic agents, antibacterial agents, anticancer agents, anticholinergic agents, anticonvulsant agents, antidepressant agents, antidiabetic agents, antidiarrheal agents, antiemetic agents, anihelminthic agents, antihistamines, antihyperlipidemic agents, antihypertensive agents, anti-infective agents, anti-inflammatory agents, antimigraine agents, antineoplastic agents, antiparkinsonism drugs, antipruritic agents, antipsychotic agents, antipyretic agents, antispasmodic agents, antitubercular agents, antiulcer agents, antiviral agents, anxiolytic agents, appetite suppressants (anorexic agents), attention deficit disorder and attention deficit hyperactivity disorder drugs, cardiovascular agents including calcium channel blockers, antianginal agents, central nervous system ("CNS") agents, beta-blockers and antiarrhythmic agents, central nervous system stimulants, diuretics, genetic materials, hormonolytics, hypnotics, hypoglycemic agents, immunosuppressive agents, muscle relaxants, narcotic antagonists, nicotine, nutritional agents, parasympatholytics, peptide drugs, protein drugs, psychostimulants, sedatives, sialagogues, steroids, smoking cessation agents, sympathomimetics, tranquilizers, vasodilators, vaccines, beta-agonist, tocolytic agents, and mixtures thereof. Each possibility represents a separate embodiment.

In one embodiment, the active pharmaceutical agent is an antibiotic or combination of antibiotics. It is known that high systemic levels of antibiotics for prolonged durations are often associated with various adverse events including, but not limited to, toxicity, decrease in gut microbiota, and development of antibiotic resistance. For example, parenteral administration of gentamicin is known to induce ototoxicity and nephrotoxicity when systemic levels exceed 10-12 µg/ml for prolonged periods of time. The composition described herein is advantageous for avoiding prolonged high levels of antibiotic(s) at the systemic level. In one embodiment, the systemic level of the antibiotic 24 hours or more after parenteral administration is less than about 10 µg/ml. In another embodiment, the systemic level of the antibiotic 24 hours or more after parenteral administration is less than about 5 µg/ml. In further embodiments, the systemic level of the antibiotic 24 hours or more after parenteral administration is less than about 1 µg/ml. For example, the systemic level of the antibiotic 24 hours or more after parenteral administration is in the range of from about 0 to about 10 µg/ml, including each integer within the specified range. In another embodiment, the systemic level of the antibiotic 24 hours or more after parenteral administration is in the range of from about 0 to about 5 µg/ml, including each integer within the specified range. In yet other embodiments, the systemic level of the antibiotic 24 hours or more after parenteral administration is in the range of from about 0 to about 1 µg/ml.

The antibiotics suitable for being incorporated into the depot system provided herein include various antibiotics, preferably having an amine moiety. Exemplary antibiotics include aminoglycoside antibiotics such as, but not limited to, kanamycin A, amikacin, tobramycin, dibekacin, gentamicin, sisomicin, netilmicin, neomycins B, C or E, and streptomycin or pharmaceutically acceptable salts thereof. Each possibility represents a separate embodiment. In one embodiment, the aminoglycoside antibiotics is gentamicin or a pharmaceutically acceptable salt thereof (e.g. gentamicin sulfate).

It is contemplated that other antibiotics are suitable for being incorporated in the composition including, but not limited to, apramycin, arbekacin, astromicin, bekanamycin, dihydrostreptomycin, elsamitrucin, fosfomycin/tobramycin, G418, hygromycin B, isepamicin, kasugamycin, legonmycin, lividomycin, micronomicin, neamine, nourseothricin, paromomycin, plazomicin, ribostamycin, streptoduocin, totomycin, verdamicin, and combinations thereof. Each possibility represents a separate embodiment. Additional antibiotics include ampicillin, norfloxacin, sulfamethoxazole, flumequine, amphotericin B, and the like. Each possibility represents a separate embodiment.

In certain aspects and embodiments, the amount of antibiotics in the pharmaceutical composition is in the range of from about 1% to about 50% (weight %), including each integer within the specified range. In one embodiment, the amount of antibiotics in the pharmaceutical composition is in the range of from about 5% to about 30% (weight %), including each integer within the specified range. Exemplary amounts include, but are not limited to, about 1%, about 5%, about 10%, about 15%, about 20%, about 25%, about 30%, about 35%, about 40%, about 45%, or about 50% (weight %), with each possibility representing a separate embodiment.

The compositions described herein may further comprise one or more pharmaceutically acceptable excipient(s) including, but not limited to, surfactants/co-surfactants, solvents/co-solvents, oily components, emulsifiers, preservatives, antioxidants, anti-foaming agents, stabilizers, buffering agents, osmotic agents, or any other excipient known in the art. Each possibility represents a separate embodiment.

Suitable surfactants/co-surfactants include, but are not limited to, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil, and the like or mixtures thereof. Each possibility represents a separate embodiment.

Suitable solvents/co-solvents include, but not limited to, alcohols, triacetin, dimethyl isosorbide, glycofurol, propylene carbonate, dimethyl acetamide, and the like or mixtures thereof. Each possibility represents a separate embodiment.

Suitable anti-foaming agents include, but are not limited to, silicon emulsions or sorbitan sesquioleate. Each possibility represents a separate embodiment.

Suitable stabilizers that may prevent or reduce the deterioration of the components in the compositions include, but are not limited to, antioxidants such as glycine, $\alpha$-tocopherol or ascorbate, butylated hydroxyanisole (BHA), butylated hydroxytulene (BHT), and the like or mixtures thereof. Each possibility represents a separate embodiment.

Suitable tonicity modifiers include, but are not limited to, mannitol, sodium chloride, and glucose. Each possibility represents a separate embodiment.

Suitable buffering agents include, but are not limited to, acetates, phosphates, and citrates with suitable cations. Each possibility represents a separate embodiment.

The parenteral compositions described herein may be prepared by any manner known in the art. In one embodiment, the active pharmaceutical agent is incorporated into the copolymer by triturating and/or mixing until a substantially homogenous composition is obtained. The composition may be inserted into ready-to-use syringes for parenteral administration. Sterilization may be effected to each of the components separately, followed by the assembly of the components under aseptic conditions to obtain the composition of the disclosure. Alternatively, sterilization may be effected to the entire composition using e.g. $\gamma$-irradiation.

In several aspects and embodiments, provided herein is a method of treating or preventing an infection, preferably osteomyelitis, the method comprising administering to a subject in need thereof any one of the compositions described herein. Within the scope of the present disclosure are methods of reducing the occurrence of osteomyelitis and/or soft tissue infection in subjects having an open bone fracture, by administration to an individual in need thereof, a therapeutically effective amount of an antibiotic in a depot form. The subject in need thereof is typically a mammal, preferably a human. The amount of a composition to be administered depends on various factors including the subject being treated (age and gender) and the severity of the disease, and can be determined by the judgment of the prescribing physician. Because of patient-to-patient variability, dosages are a guideline only and the physician may adjust doses of the compounds to achieve the level of effective treatment that the physician considers appropriate for the patient. In considering the degree of treatment desired, the physician must balance a variety of factors such as the age of the patient and the presence of other diseases or conditions. The dosing regimen ranges from a single dose administration to administration of once every few weeks or months. Depending on the duration of action required, each depot of the disclosure will typically contain between about 1 mg and about 2 g of the active agent, including each integer within the specified range. Exemplary doses include, but not limited to, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 1,500 mg, or about 2,000 mg, with each possibility representing a separate embodiment. In certain embodiments, the composition described herein contains reduced dose of the active agent relative to conventional dosage forms which are administered systemically while exerting a similar or superior therapeutic efficacy.

The term "therapeutically effective amount" or "an effective amount" as used herein refers to a quantity of a compound which is sufficient to provide a beneficial effect to the subject to which the compound is administered. The effective amount can be tested on various models both in-vitro and in-vivo.

The term "treating" as used herein refers to stopping or slowing down the progression of the disease as well as suppressing or alleviating the onset of osteomyelitis, particularly in subjects having an open bone fracture. The term "treating" further includes the reduction in the occurrence of various symptoms associated with the infection.

As used herein and in the appended claims, the term "about" refers to ±10%.

As used herein and in the appended claims, the singular forms "a", "an", and "the" include plural references unless the context clearly dictates otherwise. Thus, for example, reference to "an antibiotic" includes a combination of different antibiotics and so forth. It should be noted that the term "and" or the term "or" are generally employed in its sense including "and/or" unless the context clearly dictates otherwise.

The following examples are presented in order to more fully illustrate some embodiments of the invention. They should, in no way be construed, however, as limiting the broad scope of the invention. One skilled in the art can readily devise many variations and modifications of the principles described herein without departing from the scope of the invention.

EXAMPLES

Example 1

Formulation preparation: Gentamicin sulfate was first dried by heating at 120° C. for 1 hour. Thereafter, the dried gentamicin sulfate was incorporated into various copolymers composed of ricinoleic and sebacic acids by triturating the drug powder with the copolymer at room temperature until a homogeneous mixture was achieved. The amount of the gentamicin sulfate used was 200 mg incorporated into 800 mg of copolymer for 20% loading and 50 mg incorporated into 450 mg of copolymer for 10% loading.

Gentamicin analysis: Calibration curves of gentamicin sulfate were prepared at concentrations ranging from 2 to 16 μg/ml by reacting with 100 μl of 0.1 mg/ml fluorescamine solution in acetone and completing the volume to 1 ml using borate buffer at pH 7. Similarly, 100 μl of the collected samples from each time point was analyzed by reacting with 100 μl of 0.1 mg/ml fluorescamine solution in acetone and 800 μl borate buffer at pH 7. Thereafter, samples were incubated for 15 minutes at room temperature and the analysis of the derivate complex was performed by spectrofluorometer at excitation wavelength of 390 nm and emission wavelength of 460 nm. FIG. 1 shows the calibration curve of gentamicin.

Example 2

In-vitro release study was conducted by injecting the formulation prepared according to Example 1 with 20% gentamicin sulfate to the bottom of a centrifuge tube. Phosphate buffer saline (PBS) at pH 7.4 containing 8 g/L NaCl, 0.2 g/L KCl, and 1.15 g/L NaHPO$_4$ in DDW was used as the release medium. Tubes containing 200 mg of formulation and 5 ml of PBS were kept at 37° C. with shaking at 30 rpm until sampling. At each time point, the entire buffer solution was replaced with fresh buffer and the replaced solution was used for gentamicin content analysis as described in Example 1. The time points of replacements were: 1, 3, 7, 15, 21, 28, 35, and 42 days.

Figure 2:
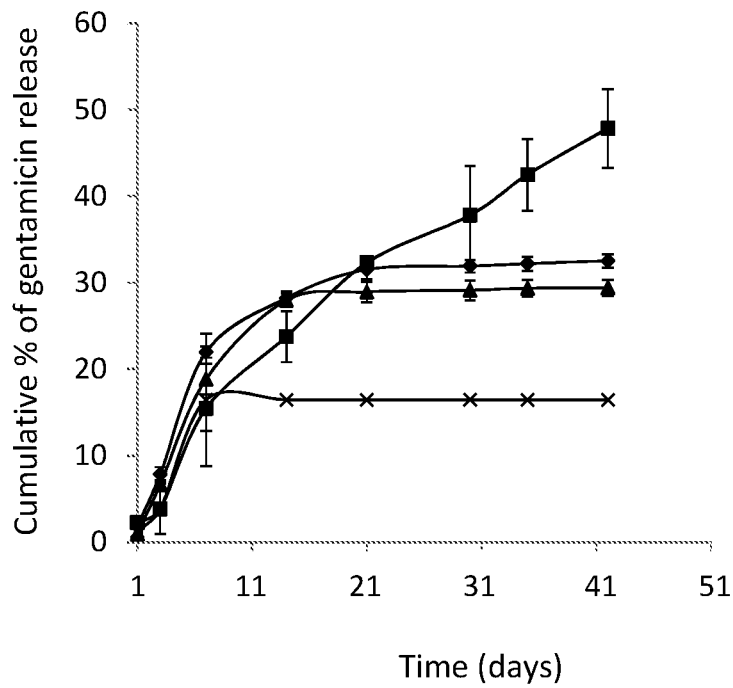
FIG. 2. In-vitro release of gentamicin from random, and alternating poly(ricinoleic acid-sebacic acid) with various ratios of ricinoleic to sebacic acid in 5 ml phosphate buffer. (■) indicates random copolymer containing ricinoleic to sebacic ratio of 70:30; (♦), (▲), and (x) indicate alternating or semi-alternating copolymer containing ricinoleic to sebacic ratios of 67:33, 70:30, and 77:23, respectively.

FIG. 2 shows the in-vitro release of gentamicin from the different formulations, where (■) indicates random copolymer containing ricinoleic to sebacic ratio of 70:30; and (♦), (▲), and (x) indicate alternating or semi-alternating copolymer containing ricinoleic to sebacic ratios of 67:33, 70:30, and 77:23, respectively. It is evident that formulations containing alternating or semi-alternating ester and anhydride bonds release a reduced cumulative amount of gentamicin from the formulation thereby affording prolonged duration of action (pharmacokinetics) of the gentamicin.

Example 3

In-vitro release study was conducted by injecting the formulation prepared according to Example 1 with 10% gentamicin sulfate to the bottom of a centrifuge tube. Tubes containing 100 mg of formulation and 1 ml of PBS were kept at 37° C. with shaking at 100 rpm until sampling. Release medium was periodically replaced with fresh buffer solution and the drug concentration was determined using spectrofluorometer as described in Example 1 at 1, 3, 5, 7, 9, 15, 21, 28, 35, and 42 days.

Figure 3:
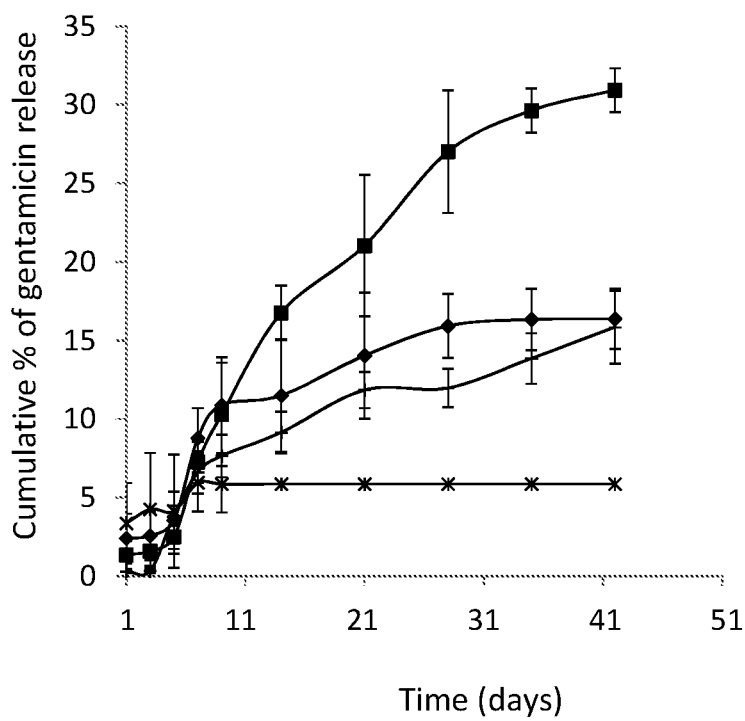
FIG. 3. In-vitro release of gentamicin from random, and alternating poly(ricinoleic acid-sebacic acid) with various ratios of ricinoleic to sebacic acid in 1 ml phosphate buffer. (■) indicates random copolymer containing ricinoleic to sebacic ratio of 70:30; (♦), (+), and (*) indicate alternating or semi-alternating copolymer containing ricinoleic to sebacic ratios of 67:33, 70:30, and 77:23, respectively.

FIG. 3 shows the in-vitro release of gentamicin from the different formulations, where (■) indicates random copolymer containing ricinoleic to sebacic ratio of 70:30; and (♦), (+), and (*) indicate alternating or semi-alternating copolymer containing ricinoleic to sebacic ratios of 67:33, 70:30, and 77:23, respectively.

The release of gentamicin from the copolymer is affected by the structure and nature of the polymer backbone. The alternating or semi-alternating polymer released gentamicin in a significantly sustained release manner after an initial burst release of up to ~10% of the drug. It is believed that the burst release pattern stems from hydrolytic cleavage of the anhydride bonds.

As seen from the figure, the alternating or semi-alternating copolymers at different ratios of ricinoleic to sebacic acids released only about 15% of the gentamicin over a period of 42 days. In contrast, the random copolymer released about twice that amount (~30%) over the same period of time. It is believed that the difference in gentamicin release from these polymers is related to the rate of cleavage of the anhydride bond where the hydrolytic degradation of copolymers leads to short oligomers that encapsulate the drug, from which it is released slowly over the period. Alternating or semi-alternating copolymer degrades into well-defined uniform ester oligomers which are contemplated to better shield the gentamicin molecules compared to non-uniform short and long ester oligomers obtained by hydrolytic degradation of random copolymer.

Example 4

In order to determine the in-vivo local and systemic release levels of gentamicin following intramuscular (IM) administration, an animal model of male New Zealand White (NZW) rabbits 3-4 months of age at study initiation (~2.5-3 kg) was used following approval from the National Council of Animal Experimentation. The test involved a single constant dose volume of 0.2 ml IM injection of a composition according to certain embodiments described herein, containing alternating or semi-alternating copolymer of ricinoleic acid and sebacic acid (70:30) and 20 wt % gentamicin sulfate. The site of injection was located at the right mid paravertebral muscle (~2.5-5 cm from the spinal cord and ~1 cm in depth) of the animals. The fur covering the paravertebral muscle was removed by close clipping using an electric clipper up to 96 hours prior to dosing. Prior to injection, a skin incision was made in order to expose the muscle. The site of injection was marked by a non-absorbable suture at the upper layer of the muscle. Injections were performed using 18-19 G needle. Following injection, the skin was closed using surgical clips. The procedure was performed under general anesthesia. Animals were clinically observed for up to 8 weeks post-dosing, if applicable. Blood samples were collected at 15 minutes, 30 minutes, 45 minutes, 1 hour, 1.5 hours, 2 hours, 4 hours, 6 hours, 8 hours, 24 hours, 48 hours, 72 hours, 1 week, 2 weeks, 3 weeks, 4 weeks, 6 weeks, and 8 weeks. Injection site and surrounding areas (muscle tissue) to assess the local gentamicin levels were collected at several time points.

Blood samples were processed by centrifugation (3,000 G for 15 minutes at room temperature). Following centrifugation, plasma was removed into plastic tubes, followed by freezing using liquid nitrogen to (−70)-(−80)° C. for subsequent analysis.

Figure 4:
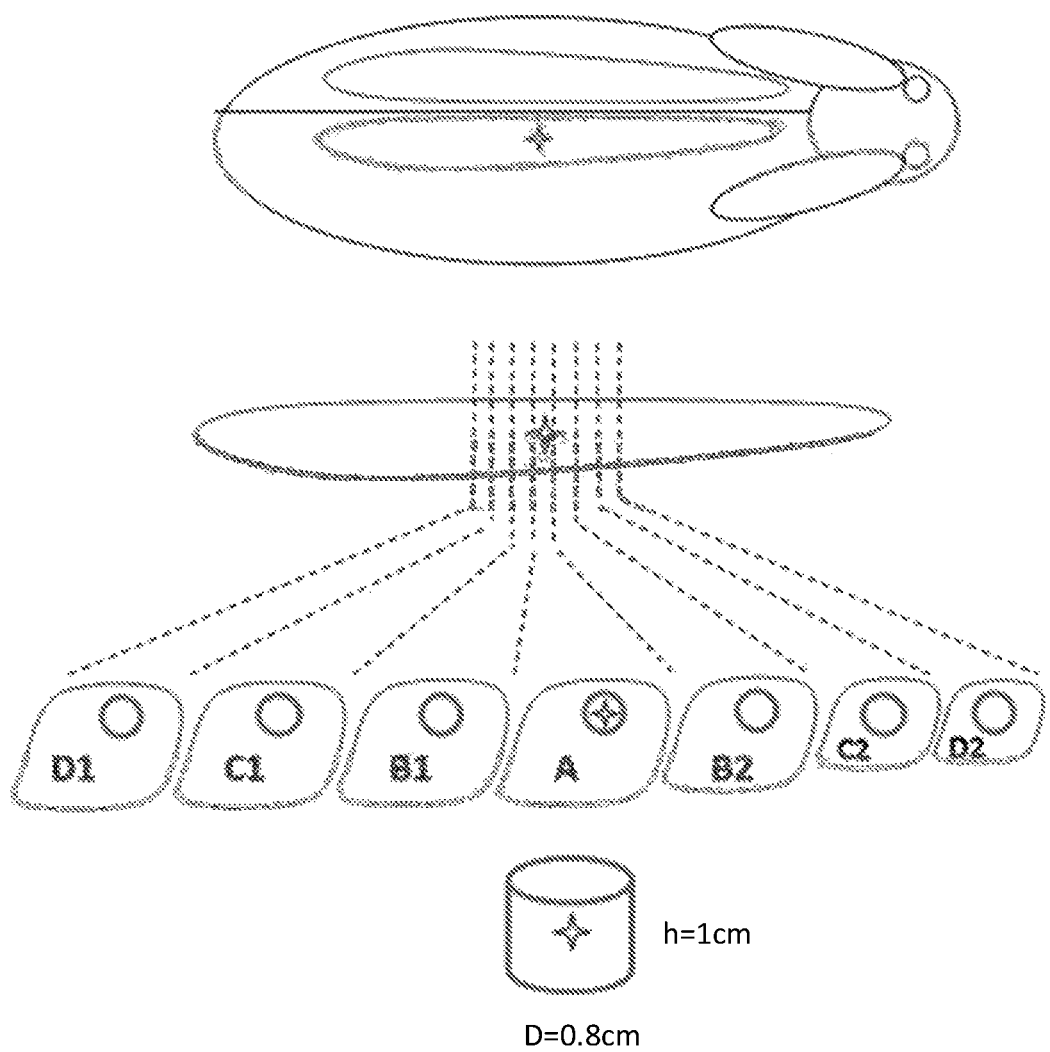
FIG. 4. A schematic illustration of the areas of measurement of local gentamicin levels following a single intramuscular injection in a rabbit.

Tissue collection was performed by resecting the right paravertebral muscle, transversally slicing into ~1 cm thick serial sections (total of 7 serial sections), when the injection site was located at the core center of the central section. Cylindrical muscle samples were obtained from each section using 0.8 cm punch biopsy, when the center of each sample was located at the horizontal plane of the injection site (i.e., 1 cm ventral to the suture) as seen in FIG. 4. At the injection site, one sample (◇) was taken. Adjacent sections of muscles were taken at the caudal and rostral to the injection site as seen in B1-2, C1-2, and D1-2 of FIG. 4.

Evaluation of gentamicin concentrations was performed as follows:

For assessing gentamicin in blood samples, 50 µl of rabbit plasma were added to 2,000 µl of MPA:MPB (MPA—1% formic acid in acetonitrile and MPB—3% formic acid in 100 nM ammonium acetate; 50:50; v/v) followed by immediate mixing by vortex, separation by centrifugation (10 minutes, 5° C., and 4,000 rpm) and filtration by 0.45 µm polypropylene filter into a glass vial with a polypropylene insert. Thereafter, the samples were injected into a LC-MS system (3 µl for samples at a concentration range of 2.5-170 µg/ml and 20 µl for samples at a concentration range of 0.075-2.5 µg/ml). For assessing gentamicin in tissue samples, 100 µl of rabbit muscle tissue sample (homogenate) were added to 2,000 µl of MPA:MPB (50:50; v/v) followed by immediate mixing by vortex, and filtration by 0.45 µm polypropylene filter into a glass vial with a polypropylene insert. Thereafter, 20 µl of the samples were injected into a LC-MS/MS system.

Calibration was performed by preparing a stock solution of gentamicin $C_1$/gentamicin $C_{1a}$/gentamicin $C_2$ (100%) in 1% formic acid in water and subsequent dilutions to achieve the desired concentration ranges. Calibration curves for gentamicin $C_1$/gentamicin $C_{1a}$/gentamicin $C_2$ were obtained by quadratic regression using the peak area of analytes vs. the nominal concentration of the calibration standards. Sample concentrations were obtained by interpolation from the run defined calibration curve. The raw data was processed using AB SCIEX 1.5.1 software.

Figure 5:
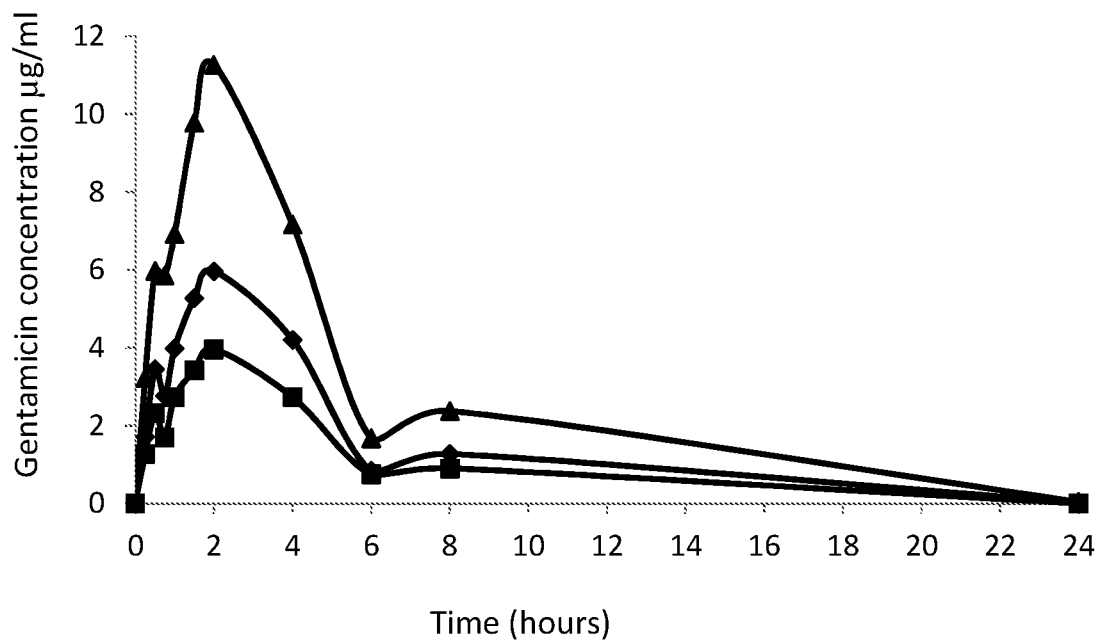
FIG. 5. Systemic gentamicin concentrations following a single intramuscular injection in a rabbit. (♦), (■), and (▲) indicate gentamicin $C_1$, gentamicin $C_{1a}$, and gentamicin $C_2$, respectively.

The results of the systemic concentration of gentamicin released are presented in FIG. 5 where (◆), (■), and (▲) indicate gentamicin $C_1$, gentamicin $C_{1a}$, and gentamicin $C_2$, respectively. Total gentamicin concentration in rabbit plasma 24 hours post administration corresponds to 0.06 µg/ml.

Figure 6:
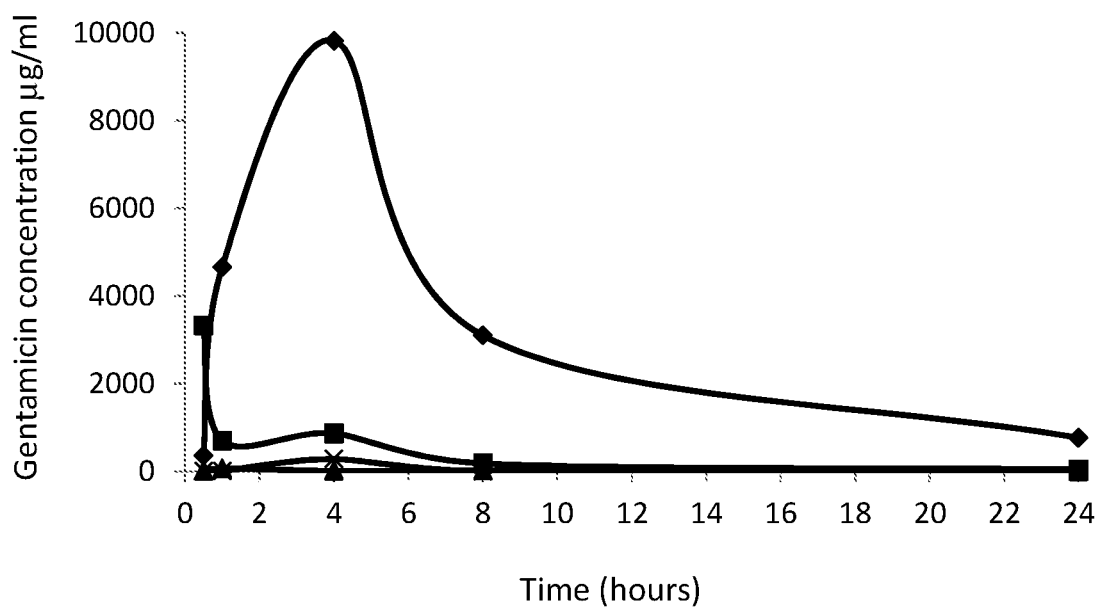
FIG. 6. Local gentamicin concentrations in areas A (♦), B (■), C (▲), and D (x) as indicated in FIG. 4 in the first 24 hours following a single intramuscular injection in a rabbit.
Figure 7:
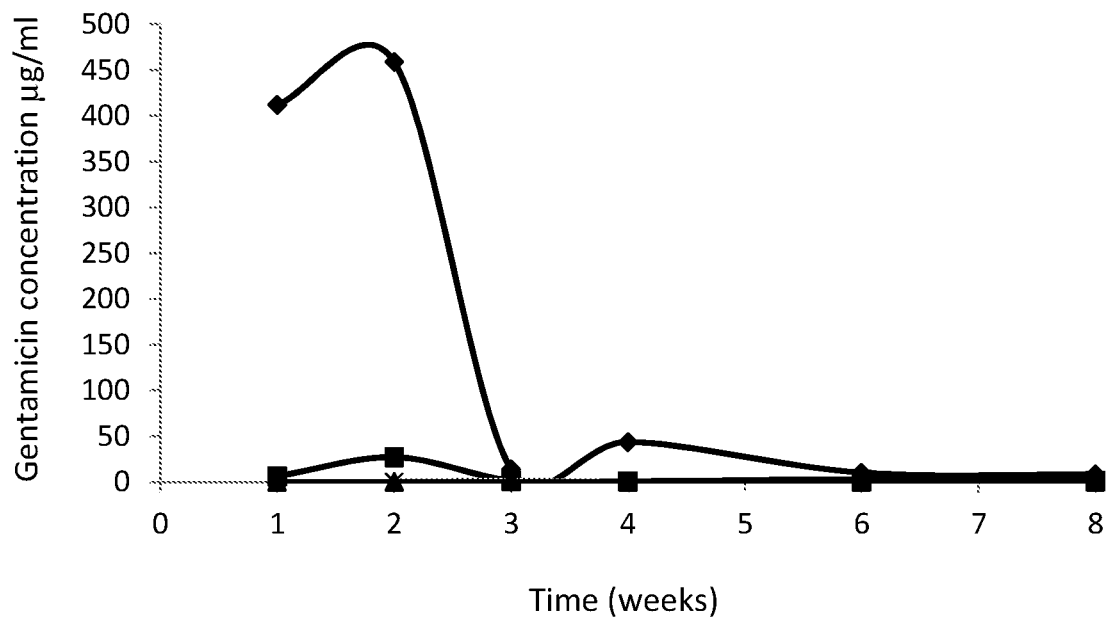
FIG. 7. Local gentamicin concentrations in areas A (♦), B (■), C (▲), and D (x) as indicated in FIG. 4 in weeks 1-8 following a single intramuscular injection in a rabbit.

The results of the local concentration of gentamicin in areas A (◆), B (■), C (▲), and D (x) (as indicated in FIG. 4) in 24 hours and 1-8 weeks are presented in FIGS. 6 and 7, respectively. The concentrations of gentamicin at 24 hours after administration are 765, 46, 3, and 6 µg/ml in areas A, B, C, and D, respectively.

Example 5

In order to determine the in-vivo local and systemic release levels of gentamicin following subcutaneous (SC) administration, an animal model of male Sprague Dawley (SD) rats 10-11 weeks of age at study initiation was used following approval from the National Council of Animal Experimentation. The test involved a single constant dose volume of 0.2 ml SC injection of a composition according to certain embodiments described herein, containing alternating or semi-alternating copolymer of ricinoleic acid and sebacic acid (70:30) and 20 wt % gentamicin sulfate. The site of injection was located at the right mid trunk area close to the spinal cord of the animals. The fur covering the flank and dorsal areas was removed by close clipping using an electric clipper up to 96 hours prior to dosing. Injections were performed using 18-19 G needle. The procedure was performed under general anesthesia. Blood samples were collected at 15 minutes, 30 minutes, 45 minutes, 1 hour, 1.5 hours, 2 hours, 4 hours, 6 hours, 8 hours, 24 hours, 48 hours, 72 hours, 1 week, 2 weeks, 3 weeks, 4 weeks, 6 weeks, and 8 weeks. Injection site and surrounding areas (skin tissue) to assess the local gentamicin levels were collected at several time points.

Blood samples were processed by centrifugation (3,000 G for 15 minutes at room temperature). Following centrifugation, plasma was removed into plastic tubes, followed by freezing using liquid nitrogen to (−70)-(−80)° C. for subsequent analysis.

Figure 8:
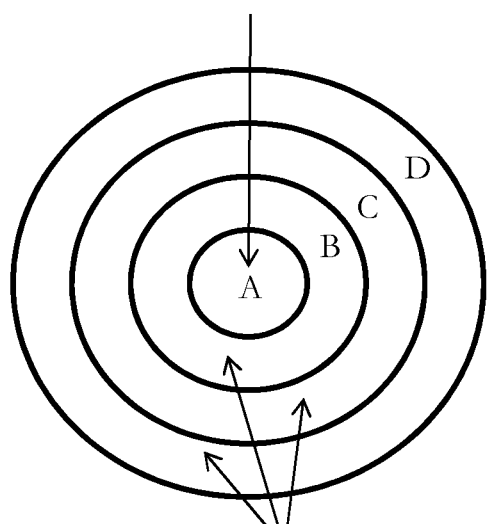
FIG. 8. A schematic illustration of the areas of measurement of local gentamicin levels following a single subcutaneous injection in a rat.

Tissue collection was performed following removal of the dorsal trunk area by close clipping using an electrical clipper, if needed. The skin at the dorsal site of the animal was removed and pinned to a cork board. Four circles of increasing size are drawn from the site of injection (identified by the presence of either the test material or a fibrotic capsule) being at 1 cm in diameter and increasing by 1 cm in diameter for each circle as seen in FIG. 8. The injection site A is marked by a circular area of 1 cm in diameter (1×0.8 cm diameter sample). Circular strips B, C, and D each indicate 0.5 cm strips in width encircling circle (at least 4 samples were taken from each strip).

Evaluation of gentamicin concentrations was performed as follows:

For assessing gentamicin in blood samples, 50 µl of rat plasma were added to 2,000 µl of MPA:MPB (MPA—1% formic acid in acetonitrile and MPB—3% formic acid in 100 nM ammonium acetate; 50:50; v/v) followed by immediate mixing by vortex, separation by centrifugation (10 minutes, 5° C., and 4,000 rpm) and filtration by 0.45 µm polypropylene filter into a glass vial with a polypropylene insert. Thereafter, the samples were injected into a LC-MS/MS system (3 µl for samples at a concentration range of 2.5-170 µg/ml and 20 µl for samples at a concentration range of 0.075-2.5 µg/ml). For assessing gentamicin in tissue samples, 100 µl of rat tissue sample (homogenate) were added to 2,000 µl of MPA:MPB (50:50; v/v) followed by immediate mixing by vortex, and filtration by 0.45 µm polypropylene filter into a glass vial with a polypropylene insert. Thereafter, 20 µl of the samples were injected into a LC-MS/MS system.

Calibration was performed by preparing a stock solution equivalent to 5,000 µg/L of gentamicin $C_1$/gentamicin $C_{1a}$/gentamicin $C_2$ (100%) in 1% formic acid in water and subsequent dilutions to achieve the desired concentration ranges. Calibration curves for gentamicin $C_1$/gentamicin $C_{1a}$/gentamicin $C_2$ were obtained by a weighed ($1/X^2$) least squares linear or quadratic regression using the peak area of analytes vs. the nominal concentration of the calibration standards. Sample concentrations were obtained by interpolation from the run defined calibration curve. The raw data was processed using AB SCIEX 1.5.1 software.

Figure 9:
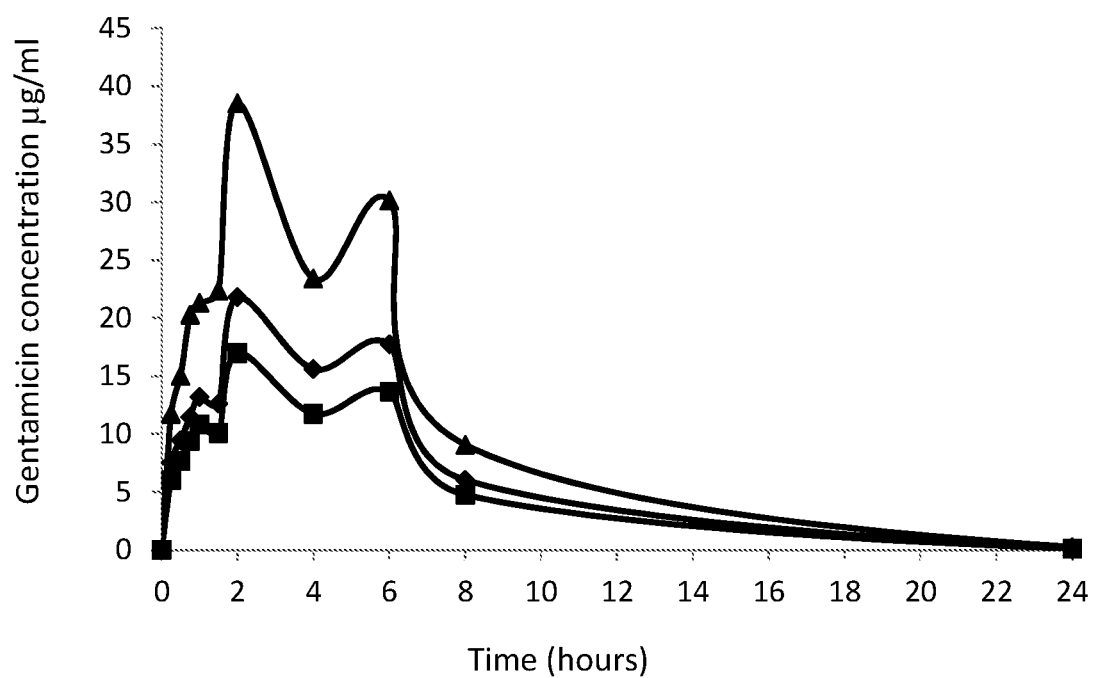
FIG. 9. Systemic gentamicin concentrations following a single subcutaneous injection in a rat. (♦), (■), and (▲) indicate gentamicin $C_1$, gentamicin $C_{1a}$, and gentamicin $C_2$, respectively.

The results of the systemic concentration of gentamicin released are presented in FIG. 9 where (♦), (■), and (▲) indicate gentamicin $C_1$, gentamicin $C_{1a}$, and gentamicin $C_2$, respectively. Total gentamicin concentration in rat plasma 24 hours post administration corresponds to 0.51 µg/ml.

Figure 10:
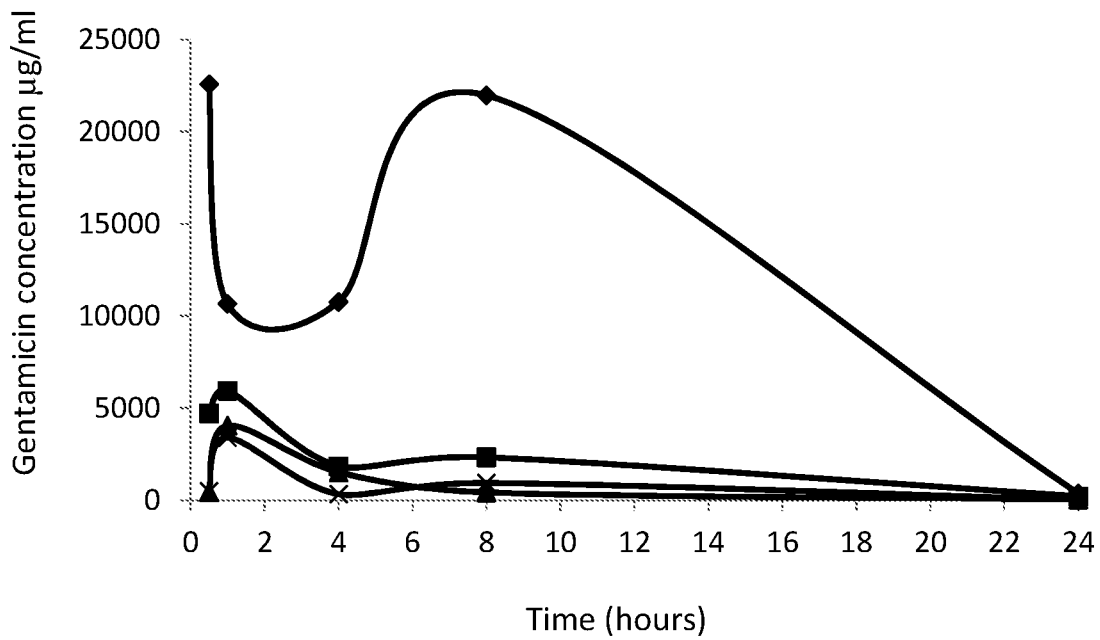
FIG. 10. Local gentamicin concentrations in areas A (♦), B (■), C (▲), and D (x) as indicated in FIG. 8 in the first 24 hours following a single subcutaneous injection in a rat.
Figure 11:
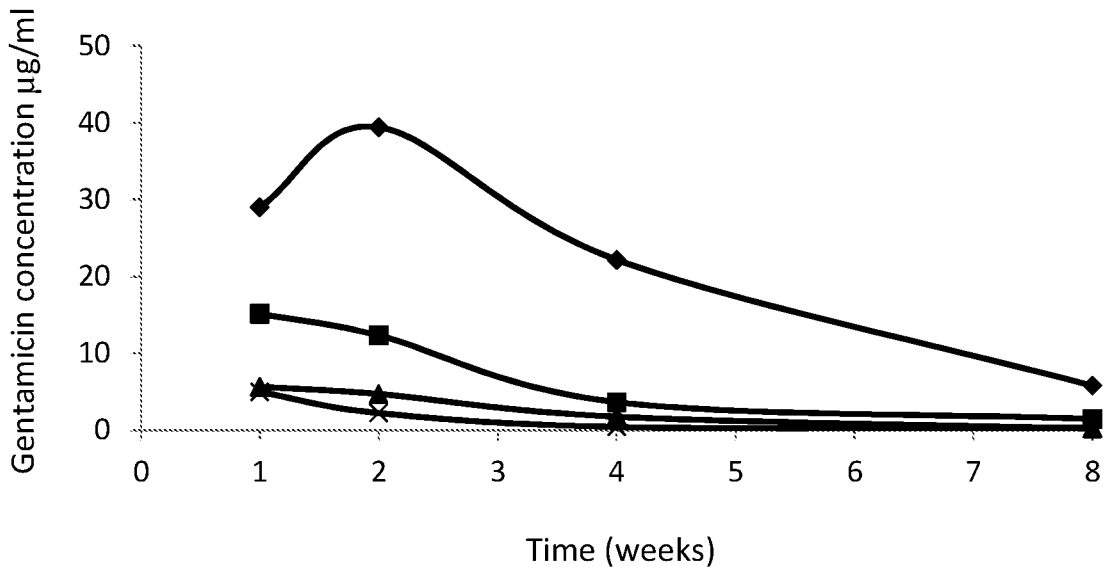
FIG. 11. Local gentamicin concentrations in areas A (♦), B (■), C (▲), and D (x) as indicated in FIG. 8 in weeks 1-8 following a single subcutaneous injection in a rat.

The results of the local concentration of gentamicin in areas A (♦), B (■), C (▲), and D (x) (as indicated in FIG. 8) in 24 hours and 1-8 weeks are presented in FIGS. 10 and 11, respectively. The concentrations of gentamicin at 24 hours after administration are 362, 218, 43, and 31 µg/ml in areas A, B, C, and D, respectively.

Example 6

In order to determine the in-vivo systemic release levels of gentamicin following intraosseous administration, an animal model of osteomyelitis was used. Male Sprague Dawley (SD) rats 10-11 weeks of age at study initiation were used following approval from the National Council of Animal Experimentation.

Animals were subjected to the following procedure: Following local anesthetics at least 30 minutes prior to surgical procedure, animals were anesthetized and the right hind limb was clipped of fur using an electric clipper. Thereafter, the clipped area was scrubbed using 4% w/v Chlorhexidine gluconate (septal scrub®) and then wiped with ethanol 70%. Longitudinal incision of the skin was made over the medial aspect of the proximal right tibia, about 1 cm in length. A cortical bone defect was produced by drilling a hole using 0.14 mm burr, just distal to the tibial tuberosity to through the cortical bone until the medullary cavity was reached. Thereafter, 19-21 G needle was introduced through the hole and along the bone to enable further insertion of the bacteria suspension and saline.

Osteomyelitis was induced by a single 20 µl insertion of bacterial suspension of *S. Aureus* to the medullary cavity of the right tibia, followed by flush with 20 µl of physiological saline. The tibial defect was closed by the use of bone wax and the skin was closed by surgical clips and polydine solution was topically applied.

Three weeks after induction of osteomyelitis, a single constant dose volume of 0.05 ml of a composition according to certain embodiments described herein, containing alternating or semi-alternating copolymer of ricinoleic acid and sebacic acid (70:30) and 20 wt % gentamicin sulfate was administered.

Blood samples at 2, 5, 8 and 24 hours after a single intraosseous (IO) administration were collected and processed by centrifugation (3,000 G for 15 minutes at room temperature). Following centrifugation, plasma was removed into plastic tubes, followed by freezing using liquid nitrogen to (−70)-(−80)° C. for subsequent analysis.

Evaluation of gentamicin concentrations was performed as follows:

For assessing gentamicin in blood samples, 50 µl of rat plasma were added to 2,000 µl of MPA:MPB (MPA—1% formic acid in acetonitrile and MPB—3% formic acid in 100 nM ammonium acetate; 50:50; v/v) followed by immediate mixing by vortex, separation by centrifugation (10 minutes, 5° C., and 4,000 rpm) and filtration by 0.45 µm polypropylene filter into a glass vial with a polypropylene insert. Thereafter, the samples were injected into a LC-MS/MS system (3 µl for samples at a concentration range of 2.5-170 µg/ml and 20 µl for samples at a concentration range of 0.075-2.5 µg/ml).

Calibration was performed by preparing a stock solution equivalent to 5,000 µg/L of gentamicin $C_1$/gentamicin $C_{1a}$/gentamicin $C_2$ (100%) in 1% formic acid in water and subsequent dilutions to achieve the desired concentration ranges. Calibration curves for gentamicin $C_1$/gentamicin $C_{1a}$/gentamicin $C_2$ were obtained by a weighed ($1/X^2$) least squares linear or quadratic regression using the peak area of analytes vs. the nominal concentration of the calibration standards. Sample concentrations were obtained by interpolation from the run defined calibration curve. The raw data was processed using AB SCIEX 1.5.1 software.

Figure 12:
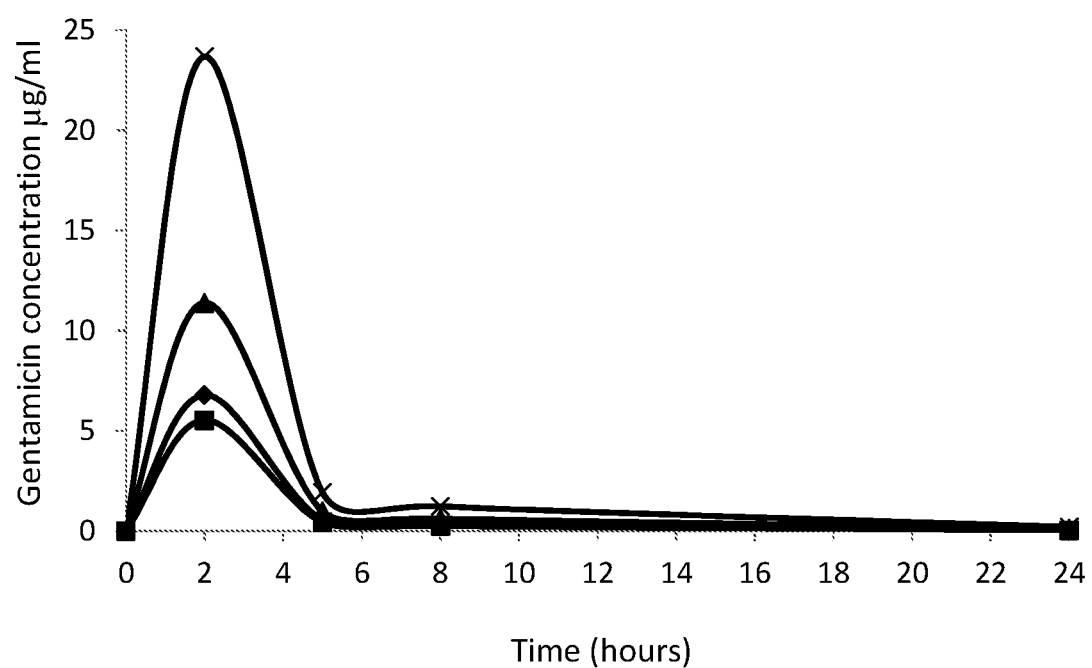
FIG. 12. Systemic gentamicin concentrations following a single intraosseous injection in a rat model of osteomyelitis. (x) indicates total gentamicin; and (♦), (■), and (▲) indicate gentamicin $C_1$, gentamicin $C_{1a}$, and gentamicin $C_2$, respectively.

The results of the systemic concentration of gentamicin released are presented in FIG. 12 where (x) indicates total gentamicin; and (♦), (■), and (▲) indicate gentamicin $C_1$, gentamicin $C_{1a}$, and gentamicin $C_2$, respectively. Total gentamicin concentration in rat plasma 24 hours post administration corresponds to 0.19 µg/ml.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A parenteral pharmaceutical composition comprising a biodegradable poly(ester-anhydride) copolymer of ricinoleic acid (RA) and sebacic acid (SA) having alternating or semi-alternating ester and anhydride bonds and an antibiotic, the composition being a sustained release depot system which releases a local therapeutically effective amount of the antibiotic over a period of about 1 day to about 20 weeks, wherein 24 hours after a single parenteral administration and throughout said period, the systemic level of the antibiotic or a metabolite thereof is about 10 µg/ml or less.

2. The pharmaceutical composition of claim 1, which releases a local therapeutically effective amount of the antibiotic over a period of about 1 week to about 8 weeks.

3. The pharmaceutical composition of claim 1, wherein 24 hours after a single parenteral administration and throughout said period, the systemic level of the antibiotic or a metabolite thereof is about 5 µg/ml or less.

4. The pharmaceutical composition of claim 3, wherein 24 hours after a single parenteral administration and throughout said period, the systemic level of the antibiotic or a metabolite thereof is about 1 µg/ml or less.

5. The pharmaceutical composition of claim 1, wherein the parenteral administration comprises subcutaneous injection.

6. The pharmaceutical composition of claim 1, wherein the parenteral administration comprises intramuscular injection.

7. The pharmaceutical composition of claim 1, wherein the parenteral administration comprises intraosseous injection.

8. The pharmaceutical composition of claim 1, wherein the parenteral administration comprises periosteal injection.

9. The pharmaceutical composition of claim 1, wherein the copolymer has a monomer ratio of ricinoleic acid to sebacic acid in the range of from about 60:40 to about 80:20 (w/w).

10. The pharmaceutical composition of claim 1, wherein the copolymer has an average molecular weight of from about 2,000 to about 50,000 daltons.

11. The pharmaceutical composition of claim 1, wherein the copolymer in the composition is degraded in vivo at a slower rate than the local or systemic release rate of the antibiotic.

12. The pharmaceutical composition of claim 1, wherein the antibiotic is an aminoglycoside.

13. The pharmaceutical composition of claim 12, wherein the aminoglycoside is gentamicin or a pharmaceutically acceptable salt thereof.

14. The pharmaceutical composition of claim 1, comprising a concentration of the antibiotic of between about 1% and about 50% (w/w).

15. The pharmaceutical composition of claim 14, comprising a concentration of the antibiotic of between about 5% and about 30% (w/w).

16. The pharmaceutical composition of claim 15, comprising a concentration of the antibiotic of about 10% (w/w) or about 20% (w/w).

17. The pharmaceutical composition of claim 1, providing reduced incidence of adverse events or reduced severity of adverse events of the antibiotic at the local or systemic level, wherein the adverse events are selected from toxicity, decrease in gut microbiota, and development of antibiotic resistance.

18. A parenteral pharmaceutical composition comprising a biodegradable poly(ester-anhydride) copolymer of ricinoleic acid (RA) and sebacic acid (SA) having alternating or semi-alternating ester and anhydride bonds and a therapeutically effective amount of gentamicin or a pharmaceutically acceptable salt thereof, the composition provides an in-vitro release of not more than about 20% of gentamicin in 25 days in 1 ml of 0.1M phosphate buffer at pH 7.4, 100 rpm and 37° C.

19. The pharmaceutical composition of claim 18, wherein the copolymer has a monomer ratio of ricinoleic acid to sebacic acid in the range of from about 60:40 to about 80:20 (w/w).

20. The pharmaceutical composition of claim 18 wherein the copolymer has an average molecular weight of from about 2,000 to about 50,000 daltons.

21. The pharmaceutical composition of claim 18, comprising a concentration of the gentamicin or a pharmaceutically acceptable salt thereof of about 10% (w/w).

\* \* \* \* \*